(12) United States Patent
Joergensen et al.

(10) Patent No.: US 8,454,577 B2
(45) Date of Patent: *Jun. 4, 2013

(54) CATHETER HAVING AN AUXILIARY LUMEN FOR USE WITH A FUNCTIONAL MEASUREMENT WIRE

(75) Inventors: Ib Erling Joergensen, Haigerloch (DE); Randolf Von Oepen, Los Altos, CA (US)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 13/316,303

(22) Filed: Dec. 9, 2011

(65) Prior Publication Data

US 2012/0143089 A1 Jun. 7, 2012

Related U.S. Application Data

(60) Continuation of application No. 12/652,650, filed on Jan. 5, 2010, now Pat. No. 8,075,549, which is a continuation of application No. 11/390,327, filed on Mar. 27, 2006, now Pat. No. 7,645,260, which is a division of application No. 10/391,713, filed on Mar. 18, 2003, now Pat. No. 7,018,358.

(51) Int. Cl.
*A61M 31/00* (2006.01)

(52) U.S. Cl.
USPC .......................................................... 604/523

(58) Field of Classification Search
USPC .................. 604/96.01, 97, 98, 100, 101, 102, 604/103.4, 534, 535, 284; 606/191–194
See application file for complete search history.

(56) References Cited

U.S. PATENT DOCUMENTS

| | | | |
|---|---|---|---|
| 5,188,621 A | 2/1993 | Samson | |
| 5,201,315 A | 4/1993 | Griffith | |
| 5,203,338 A | 4/1993 | Jang | |
| 5,531,700 A | 7/1996 | Moore et al. | |
| 5,824,173 A | 10/1998 | Fontirroche et al. | |
| 5,921,971 A | 7/1999 | Agro et al. | |
| 6,066,100 A | 5/2000 | Willard et al. | |
| 6,193,669 B1 | 2/2001 | Degany et al. | |
| 6,299,595 B1 | 10/2001 | Dutta et al. | |
| 6,475,187 B1 | 11/2002 | Gerberding | |
| 7,018,358 B2 | 3/2006 | Joergensen et al. | |
| 7,645,260 B2 * | 1/2010 | Joergensen et al. | 604/96.01 |
| 8,075,549 B2 | 12/2011 | Joergensen et al. | |
| 2002/0128596 A1 | 9/2002 | Stivland et al. | |

FOREIGN PATENT DOCUMENTS

EP 1201260 5/2002

OTHER PUBLICATIONS

U.S. Appl. No. 10/391,713, filed May 18, 2004, Office Action.
U.S. Appl. No. 10/391,713, filed Apr. 19, 2005, Office Action.
U.S. Appl. No. 10/391,713, filed Oct. 18, 2005, Notice of Allowance.
U.S. Appl. No. 10/391,713, filed Mar. 8, 2006, Issue Notification.
U.S. Appl. No. 11/390,327, filed Mar. 30, 2009, Office Action.
U.S. Appl. No. 11/390,327, filed Jul. 13, 2009, Notice of Allowance.
U.S. Appl. No. 11/390,327, filed Dec. 23, 2009, Issue Notification.
U.S. Appl. No. 12/652,650, filed Sep. 8, 2010, Office Action.
U.S. Appl. No. 12/652,650, filed Aug. 9, 2011, Notice of Allowance.

* cited by examiner

*Primary Examiner* — Manuel Mendez
(74) *Attorney, Agent, or Firm* — Workman Nydegger; Jonathan D. Feuchtwang

(57) ABSTRACT

The present invention relates to a surgical catheter, and more particularly, a balloon catheter having an auxiliary lumen configured to permit the advancement of a functional measurement wire to a treatment site. The auxiliary lumen communicates with a working lumen that is configured to permit the advancement of a guidewire and the functional measurement wire, so that the guidewire and functional measurement wire may selectively be advanced to the treatment site during a surgical procedure.

20 Claims, 7 Drawing Sheets

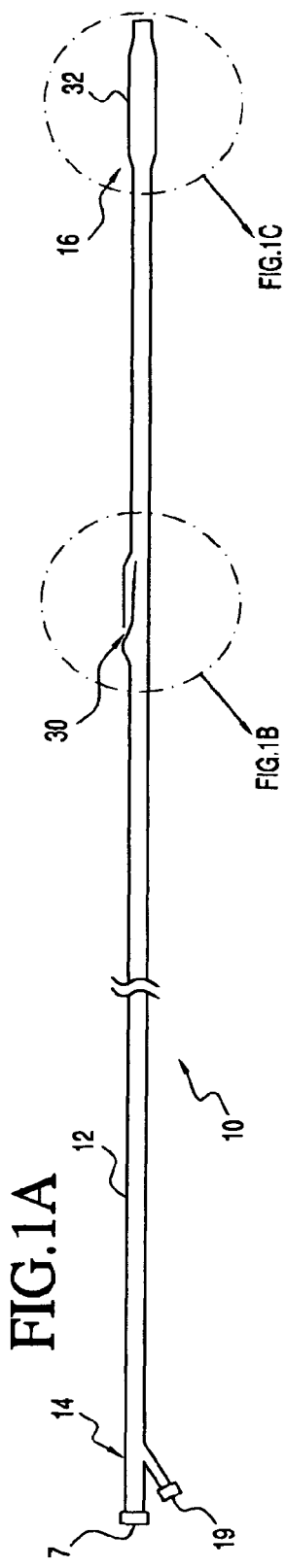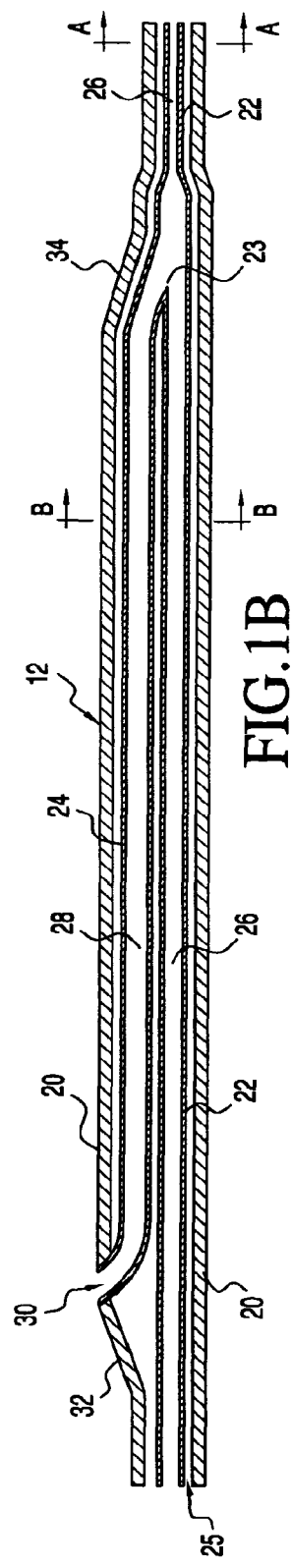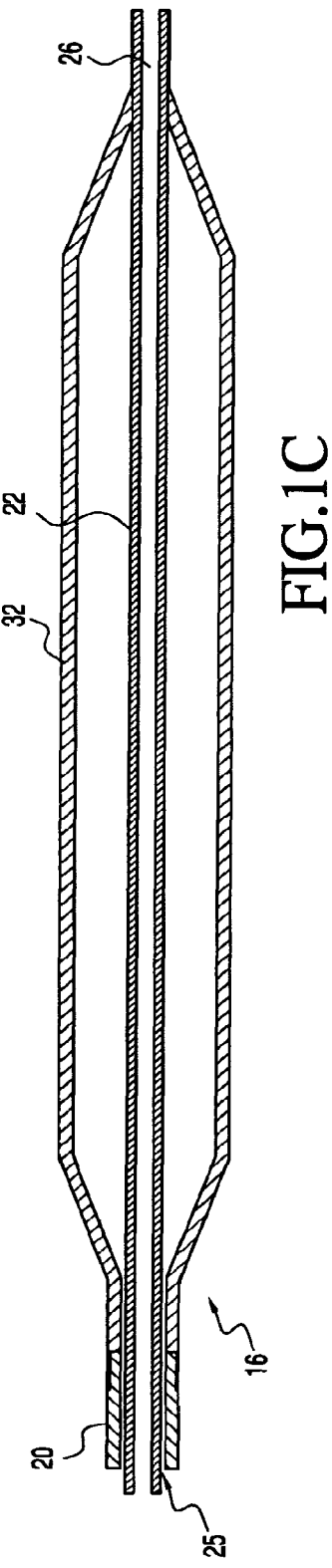

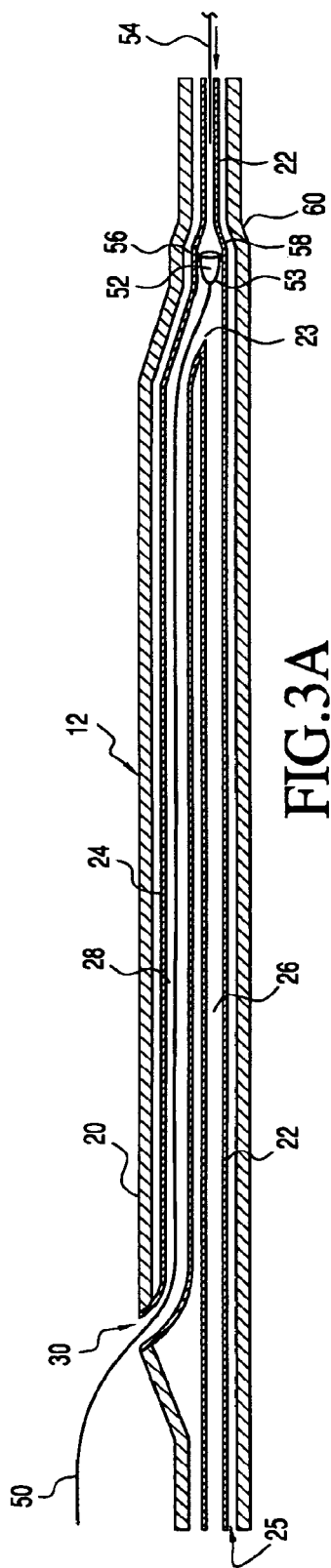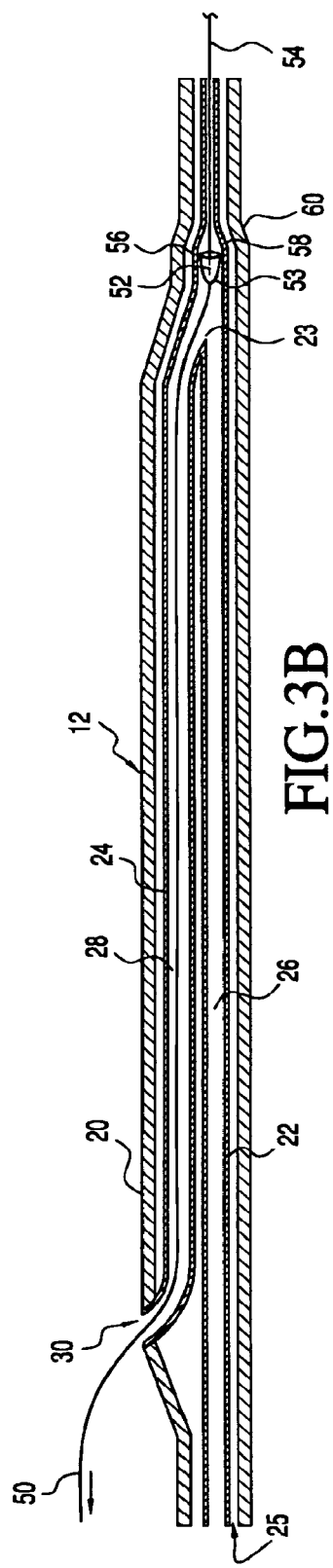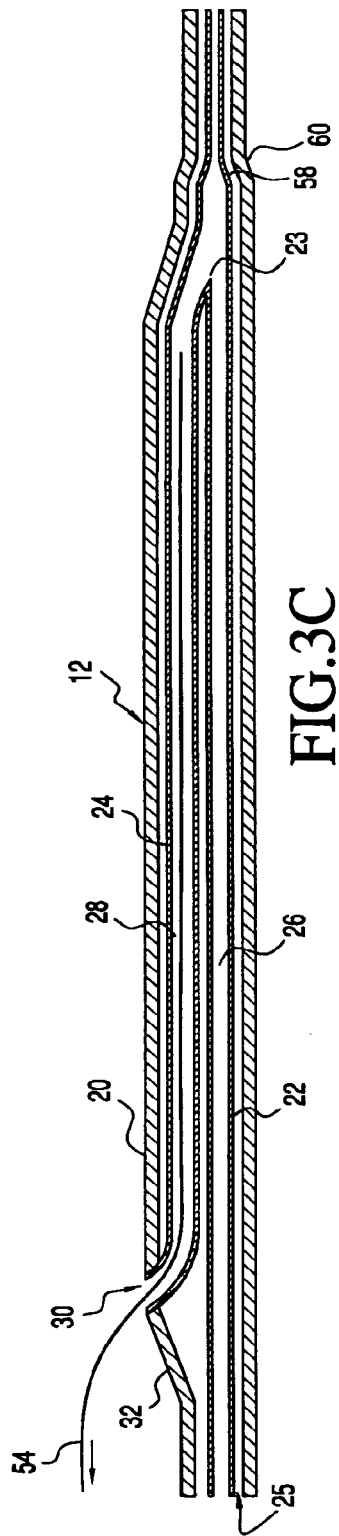

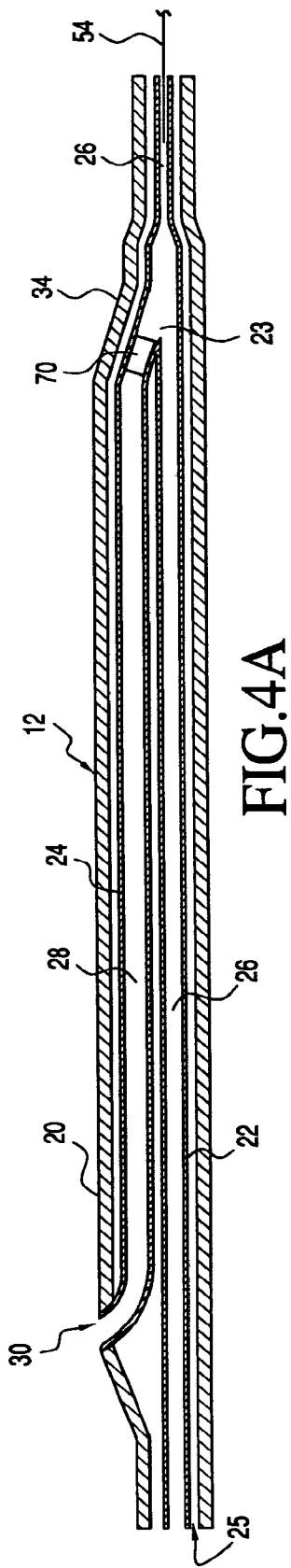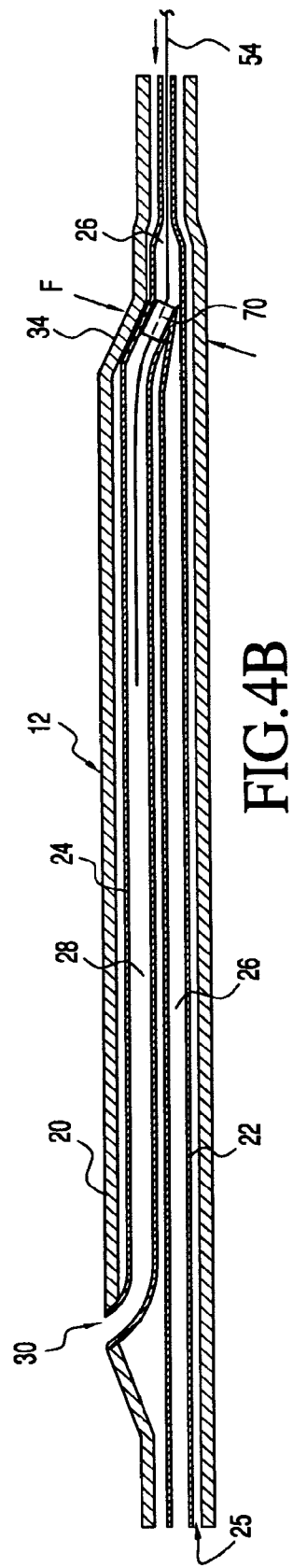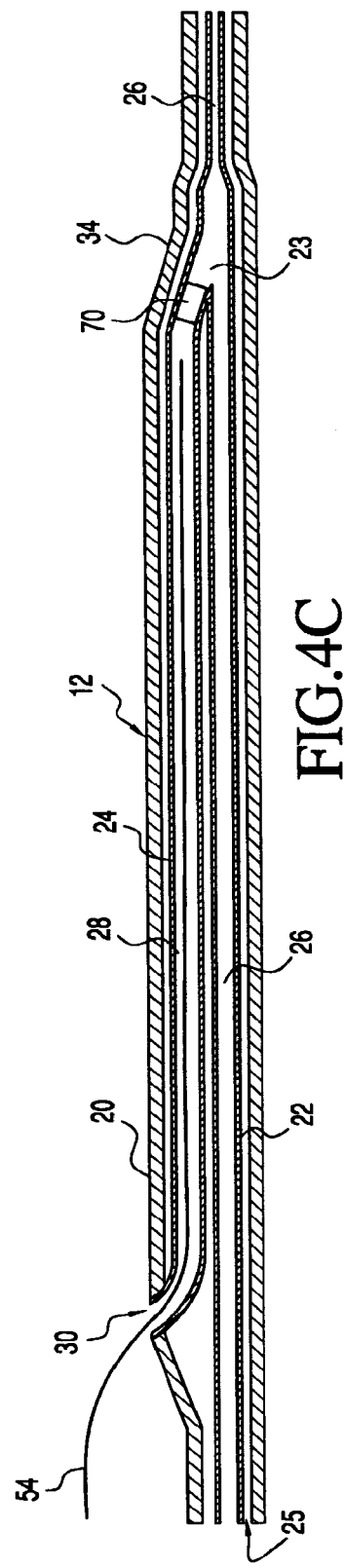

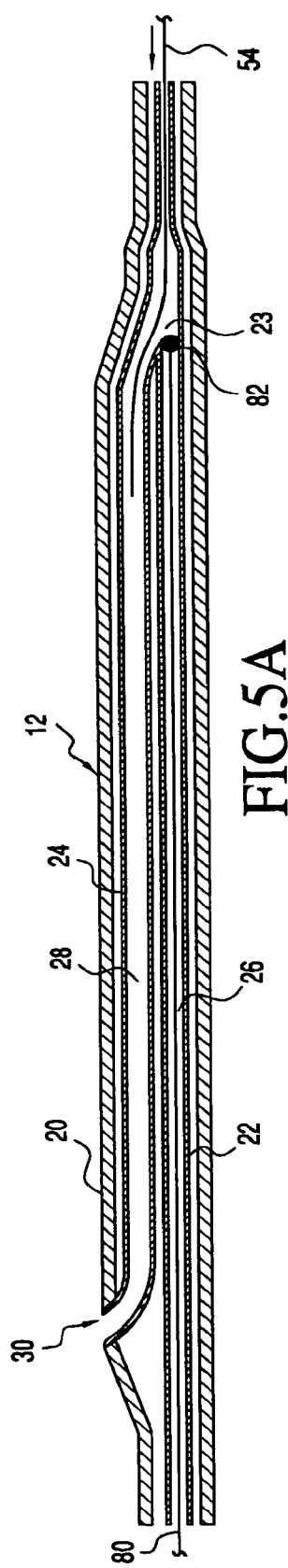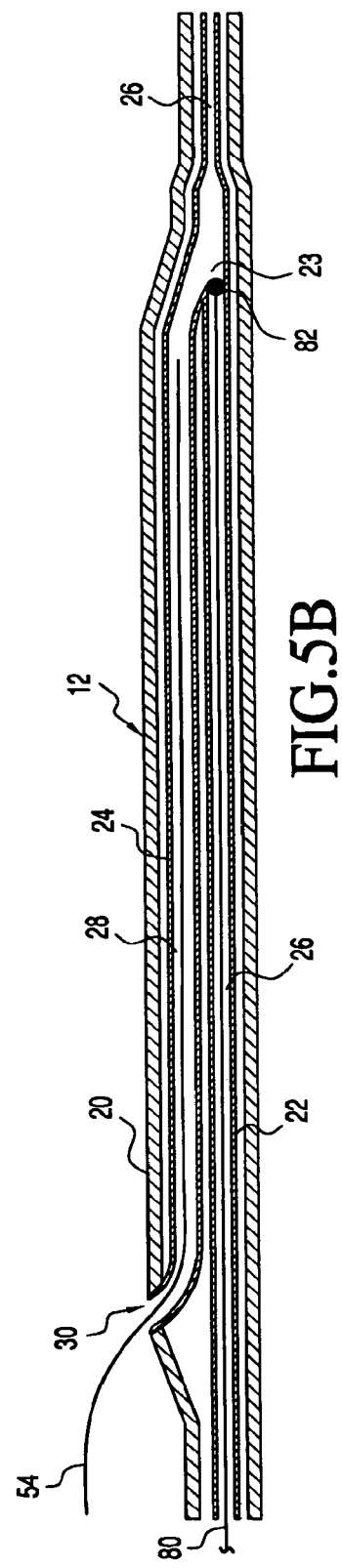

CATHETER HAVING AN AUXILIARY LUMEN FOR USE WITH A FUNCTIONAL MEASUREMENT WIRE

This application is a continuation of U.S. patent application Ser. No. 12/652,650 filed Jan. 5, 2010, issued as U.S. Pat. No. 8,075,549, which is a continuation of U.S. patent application Ser. No. 11/390,327 filed Mar. 27, 2006, issued as U.S. Pat. No. 7,645,260, which is a divisional of U.S. patent application Ser. No. 10/391,713 filed Mar. 18, 2003, issued as U.S. Pat. No. 7,018,358, the entireties of which are hereby incorporated by reference.

FIELD OF THE INVENTION

The present invention relates to a surgical catheter, and more particularly, a balloon catheter having an auxiliary lumen configured to permit the advancement of a functional measurement wire to a treatment site.

BACKGROUND OF THE INVENTION

Balloon angioplasty is a widely used technique for treating vascular disease. In balloon angioplasty, a catheter having an inflatable balloon affixed to its distal end is guided through a patient's vasculature with the balloon in a deflated state, and the balloon is positioned within a vascular lesion. The balloon then is inflated to compress the atherosclerotic plaque against the vessel wall to restore adequate blood flow in the vessel.

It may be desirable to obtain various physiological measurements near the treatment site before, during or after an intravascular surgical procedure, such as balloon angioplasty. For example, it may be useful to obtain pressure or flow measurements near the site of a vascular occlusion. It may be beneficial to readily obtain such measurements at any time during the surgical procedure to assess the efficacy of the procedure.

One previously known method of placing a functional measurement wire at a treatment site is to exchange the functional measurement wire for the guide wire, i.e., to fully withdraw the guide wire from the vessel and then insert the functional measurement wire in place of the guide wire. Once the measurement is taken, the functional measurement wire is withdrawn and the guidewire reinserted. Such a method can be cumbersome and time-consuming, especially where it is desired to take multiple measurements during the course of a procedure.

Alternatively, a separate lumen may be provided in the catheter to accommodate the functional measurement wire, but this solution requires an increase in the catheter profile. Such an increase in profile, especially at the distal end of the catheter, may undesirably limit applicability of the device in smaller vessels, and also may result in an increase in the stiffness of the distal region of the catheter, thereby making it more difficult to negotiate tortuous anatomy.

Other alternative approaches are known in the art. For example, U.S. Pat. No. 5,921,957 to Killion et al. describes a balloon dilatation catheter having a guidewire lumen, and an atraumatic tip at the distal end of the catheter having an aperture that the guidewire passes through. The diameter of the aperture matches the diameter of the guidewire used in the procedure. The inner diameter of the guidewire lumen is described as substantially larger than the guidewire diameter used in the procedure, which creates a space between the guidewire and the guidewire lumen. In this available space, dye injections and pressure measurements may be performed via holes in the atraumatic tip that are disposed just proximal to the aperture. Accordingly, when the guidewire extends through the aperture, pressure measurements may be obtained via the extra space provided in the guidewire lumen and the holes in the atraumatic tip.

A main drawback associated with the device described in the Killion patent is that, in order to take pressure measurements through the guidewire lumen, the guidewire lumen must be relatively large to provide the additional lumen space that is required. By increasing the inner diameter of the guidewire lumen, the stiffness of the device is undesirably increased, and may render the device unsuitable for use in smaller vessels.

Still other previously-known devices have incorporated the use of a slit, port or frangible wall disposed in a lateral surface of the catheter that communicates with a guidewire lumen. For example, U.S. Pat. No. 5,921,971 to Agro et al. describes a catheter having a guidewire lumen extending along the catheter, wherein a slit in the catheter shaft allows a guidewire to be introduced into the guidewire lumen. The catheter further comprises two ancillary lumens that extend longitudinally along the length of the catheter.

One drawback associated with the device described in the Agro patent is that the guidewire may not be easily used in combination with other devices, such as a functional measurement wire, without removing the guidewire from the side slit and then introducing the measurement wire. Although the functional measurement wire alternatively may be introduced into one of the ancillary lumens, an increase in catheter profile occurs when providing a guidewire and functional measurement wire simultaneously at the distal end of the catheter.

In view of these disadvantages of previously known catheters, it would be desirable to provide a catheter that may be used in conjunction with a functional measurement wire to obtain measurements near a vascular treatment site.

It also would be desirable to provide a catheter that readily may introduce either a guidewire or a functional measurement wire to a vascular treatment site.

It further would be desirable to provide a catheter that readily may advance either a guidewire or a functional measurement wire to a vascular treatment site while maintaining a minimal distal catheter profile.

SUMMARY OF THE INVENTION

In view of the foregoing, it is an object of this invention to provide a catheter that may be used in conjunction with a functional measurement wire to obtain measurements near a vascular treatment site.

It is also an object of this invention to provide a catheter that readily may introduce either a guidewire or a functional measurement wire to a vascular treatment site.

It is a further object of the present invention to provide a catheter that readily may advance either a guidewire or a functional measurement wire to a vascular treatment site while maintaining a minimal distal catheter profile.

These and other objects of the present invention are accomplished by providing a balloon catheter having an auxiliary lumen configured to permit a functional measurement wire to be selectively advanced to a treatment site. The auxiliary lumen communicates with a working lumen, and is configured to permit the advancement of either a guidewire or the functional measurement wire.

In a preferred embodiment, the apparatus comprises a catheter having an outer tube and an inner tube, each having proximal and distal ends. The inner tube comprises a working lumen extending therethrough and is disposed within the outer tube along the length of the catheter. The apparatus further comprises an auxiliary tube having an auxiliary lumen that is in communication with a side port disposed in a lateral surface of the outer tube near the distal end. The distal end of the auxiliary lumen communicates with the working lumen via a bifurcation. The apparatus further preferably comprises an inflatable member disposed at the distal end of the catheter that is in fluid communication with an inflation lumen formed between the inner tube and the outer tube.

The auxiliary lumen is configured to permit the selective advancement of a functional measurement wire to a treatment site via a distal portion of the working lumen. In a preferred method, a proximal end of the functional measurement wire is loaded into the distal portion of the working lumen, then directed into the auxiliary lumen. The functional measurement wire then is retracted proximally until a distal end of the functional measurement wire is positioned within the auxiliary lumen, preferably at a location just proximal of the bifurcation between the auxiliary lumen and the working lumen. A proximal portion of the functional measurement wire extends out of the side port in the outer tube and resides in the vessel, with the proximal end of the functional measurement wire disposed outside the patient's body for manipulation by the physician.

During a medical procedure, the catheter is advanced over a guidewire, via the working lumen of the catheter, to a treatment site. The guidewire then may be retracted proximally, so that its distal end is disposed proximal of the bifurcation. The functional measurement wire then may be advanced distally to the treatment site via the distal portion of the working lumen. The functional measurement wire accordingly may be advanced to the treatment site to take desired measurements, for example, pressure or flow measurements, before, during or after an intravascular procedure, without a full exchange of the guide wire and without the need for a separate lumen for the functional measurement wire in the proximal portion of the catheter.

Methods of loading the functional measurement wire into the auxiliary lumen prior to the intravascular procedure, so that the functional measurement wire readily may be advanced to a treatment site during the procedure, also are provided.

BRIEF DESCRIPTION OF THE DRAWINGS

Further features of the invention, its nature and various advantages will be apparent from the accompanying drawings and the following detailed description of the preferred embodiments, in which:

FIGS. 1A-1C are, respectively, a side view of the apparatus of the present invention, and side sectional views of central and distal portions of the apparatus;

FIGS. 3A-3C are side sectional views depicting a method for loading a functional measurement wire into an auxiliary lumen of the present invention;

FIGS. 4A-4C are side sectional views depicting an alternative method for loading a functional measurement wire into an auxiliary lumen of the present invention;

FIGS. 5A-5B are side sectional views depicting yet a further alternative method for loading a functional measurement wire into an auxiliary lumen of the present invention;

DETAILED DESCRIPTION OF THE INVENTION

Figure 2B:
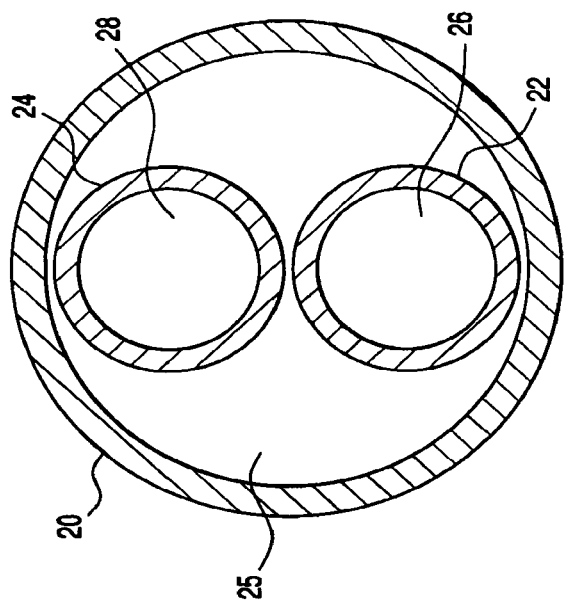
FIGS. 2A-2B are, respectively, cross-sectional views along line A-A and line B-B of FIG. 1B.

The present invention is directed to a therapeutic catheter, such as a balloon angioplasty catheter or stent delivery system, and methods that allow the advancement of a functional measurement wire to a treatment site using an auxiliary lumen of the catheter. In accordance with the principles of the present invention, the catheter comprises an outer tube, and an inner tube disposed within the outer tube that bifurcates from a working lumen into an auxiliary lumen configured to permit the advancement of the functional measurement wire. Because the auxiliary lumen merges with the working lumen, the functional measurement wire may be introduced before, during or after a surgical procedure in a convenient manner without causing an increased distal catheter profile.

Referring to FIG. 1, apparatus 10 of the present invention preferably comprises balloon catheter 12 having proximal end 14 and distal end 16. Balloon catheter 12 comprises outer tube 20 and inner tube 22, each having proximal and distal ends, as shown in FIG. 1B. Inner tube 22 is disposed within outer tube 20, and the annulus between outer tube 20 and inner tube 22 forms inflation lumen 25. Inner tube 22 comprises working lumen 26 that extends from proximal end 14 of catheter 12 to distal end 16. At proximal end 14, working lumen 26 is coupled to guidewire port 17, while inflation lumen 25 is coupled to inflation port 19. Guidewire port 17 and inflation port 19 may be constructed in manners that are per se known in the art.

In accordance with principles of the present invention, inner tube 22 includes bifurcation 23 where inner tube 22 converges with auxiliary tube 24. Auxiliary tube 24 has proximal and distal ends and auxiliary lumen 28 extending therethrough. Auxiliary lumen 28 is in communication with working lumen 26 of inner tube 22 at the distal end, while the proximal end of auxiliary lumen 28 is in communication with side port 30, which is disposed in a lateral surface of outer tube 20, as shown in FIG. 1B.

As described in detail with respect to FIGS. 6-7 hereinbelow, auxiliary lumen 28 is sized to permit the advancement of a functional measurement wire, e.g., a wire having a pressure or flow sensor disposed at a distal end. Working lumen 26 comprises a proximal portion disposed proximal of bifurcation 23, and a distal portion disposed distal of bifurcation 23, as shown in FIG. 1B. The proximal portion of working lumen 26 is sized to permit the advancement of a guidewire, while the distal portion is sized to permit the advancement of either a guidewire or a functional measurement wire to the site of an occlusion.

The distal end of inner tube 22 preferably is affixed to a distal end of balloon 32, as shown in FIG. 1C, while a proximal end of balloon 32 is affixed to the distal end of outer tube 20. Occlusion balloon 32 may be constructed in accordance with balloon catheters that are per se known in the art, e.g., using a compliant or semi-compliant material, such as polyurethane, latex or polyisoprene. Additionally, inner tube 22 may comprise at least one radiopaque marker (not shown) that is disposed within balloon 32 to facilitate positioning of distal end 16 in a patient's vasculature.

Figure 2A:
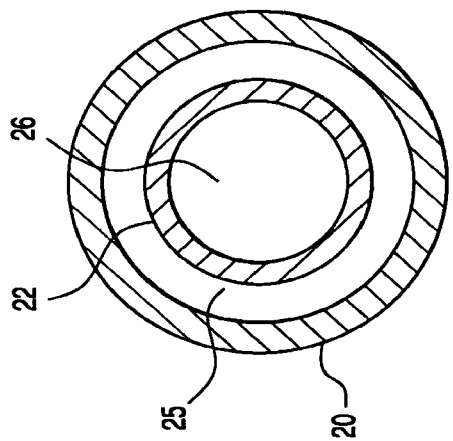

Referring to FIG. 2, two cross-sectional views of catheter 12 are provided. FIG. 2A depicts a cross-sectional view along line A-A of FIG. 1B, wherein inner tube 22 is disposed within outer tube 20. Inner tube 22 comprises working lumen 26 that is sized to permit selective longitudinal advancement of either a guidewire or a functional measurement wire. An annulus between inner tube 22 and outer tube 20 forms inflation lumen 25.

In FIG. 2B, a cross-sectional view along line B-B of FIG. 1B is provided, wherein inner tube 22 and auxiliary tube 24 are disposed within outer tube 20. Spaces between outer tube 20, inner tube 22 and auxiliary tube 24 form inflation lumen 25 in this region. Auxiliary tube 24 comprises auxiliary lumen 28 that is sized to permit the longitudinal advancement of a functional measurement wire.

In a preferred embodiment of the present invention, the outer diameter of outer tube 20 along section A-A is about 2.7 F (about 0.9 mm), while the outer diameter of outer tube 20 along section B-B is about 3.2 F (about 1.05 mm). As shown in FIG. 1B, outer tube 20 preferably comprises proximal taper 32 and distal taper 34 to accommodate the additional diameter provided by auxiliary tube 24.

Lumen 26 preferably is sized to accommodate a standard 0.014 in. (0.36 mm) guidewire, while auxiliary lumen may be sized to accept a previously-known functional measurement wire, such as the FloWire® flow measurement wire or WaveWire® pressure measurement wire offered by Jomed, Inc., Rancho Cordova, Calif. Auxiliary lumen 28 preferably has a length, e.g., 5 to 10 cm, sufficient to prevent the distal end of the functional measurement wire from slipping out of the auxiliary lumen when the distal end of the functional measurement wire is parked therein.

Catheter 10 may in addition comprise a stylet, discussed below with respect to FIGS. 3 and 4, to facilitate initial placement of the functional measurement wire in the auxiliary lumen.

Referring now to FIG. 3, a preferred method of using catheter 12 in combination with a functional measurement wire is described. In a first step, stylet 50 having proximal and distal ends and receptor 52 coupled to the distal end is partially disposed within auxiliary lumen 28, as shown in FIG. 3A. The distal end of stylet 50, including receptor 52, is loaded into region 56 of inner tube 22, which is situated just distal to bifurcation 23. Region 56 comprises a slightly larger inner diameter relative to the inner diameter of working lumen 26, to accommodate for the bifurcation from working lumen 26 into two separate lumens. Outer tube 20 and inner tube 22 preferably comprise circumferential tapers 60 and 58, respectively, that provide a transition to the slightly larger diameter at region 56.

When receptor 52 is disposed within region 56 of inner tube 22, the proximal end of stylet 50 exits auxiliary lumen 28 at side port 30 of outer tube 20, as shown in FIG. 3A. This enables a physician to manipulate the proximal end of stylet 50, while the distal end having receptor 52 remains disposed within region 56. In a preferred embodiment, an outer portion of receptor 52 is sized to engage an inner wall of region 56 so that minimal friction holds receptor 52 in place, but so that relatively small forces may overcome the friction and proximally retract receptor 52.

In a next step, functional measurement wire 54 having proximal and distal ends is provided. As shown in FIG. 3A, the proximal end of functional measurement wire 54 is loaded into the distal portion of working lumen 26 at the distal end of catheter 12. The proximal end of functional measurement wire 54 then is advanced proximally within the distal portion of working lumen 26 until it engages an inner surface of receptor 52, as shown in FIG. 2B. The inner surface of receptor 52 may comprise an adhesive or mechanical engagement configured to engage the proximal end of functional measurement wire 54. Once engaged, a physician may retract an exposed portion of stylet 50 proximally, which in turn will proximally retract receptor 52 and functional measurement wire 54. Receptor 52 may comprise proximal taper 53 that ensures that receptor 52 does not snag at bifurcation 23, but rather is guided smoothly into auxiliary lumen 28.

Once the distal end of functional measurement wire 54 has been guided into auxiliary lumen 28, as shown in FIG. 3C, the proximal end of functional measurement wire 54 may be disengaged from the inner surface of receptor 52 and coupled to its appropriate measurement circuitry. Functional measurement wire 54 is thus parked within auxiliary lumen 28 so that it readily may be advanced in a distal direction into the distal portion of working lumen 26, and extended into a vascular treatment site to obtain desired measurements.

Referring to FIG. 4, an alternative method for loading functional measurement wire 54 into auxiliary lumen 28 is described. In FIG. 4A, catheter 12 comprises tubular member 70 that preferably is fixedly disposed substantially within a region of taper 34, and provides a transition between the distal portion of working lumen 26 and auxiliary lumen 28, as shown in FIG. 4A.

In FIG. 4A, the proximal end of functional measurement wire 54 is loaded into the distal portion of working lumen 26 at distal end 16 of catheter 12. The proximal end of functional measurement wire 54 then is advanced proximally within the distal portion of catheter 12. When the proximal end of functional measurement wire 54 is just distal to bifurcation 23, a portion of outer tube 20 near taper 34 may be compressed, e.g., manually, as shown in FIG. 4B. Compressive force F may be sufficient to collapse a local portion of working lumen 26 without displacing tubular member 70, which preferably is relatively rigid. This effectively closes bifurcation 23 and causes the distal portion of working lumen 26 to communicate exclusively with auxiliary lumen 28, as shown in FIG. 4B.

The proximal end of functional measurement wire 54 then may be been guided through tubular member 70 into auxiliary lumen 28, and compressive force F may be removed so catheter 12 returns to its original shape of FIG. 4A. Functional measurement wire 54 then may be retracted proximally until the distal end of functional measurement wire 54 is disposed just proximal of bifurcation 23, as shown in FIG. 4C. In use, functional measurement wire 54 readily may be advanced in a distal direction through tubular member 70 and into the distal portion of working lumen 26, then extended into treatment site near the distal end of catheter 12.

Referring to FIG. 5, a further alternative method for loading functional measurement wire 54 into auxiliary lumen 28 is described. In FIG. 5A, stylet 80 having proximal and distal ends and guiding member 82 coupled to the distal end is provided in the proximal portion of working lumen 26. The distal end of stylet 80 is loaded into the proximal portion of working lumen 26 and is advanced distally so that guiding member 82 preferably is disposed just proximal to bifurcation 23, as shown in FIG. 5A.

The proximal end of functional measurement wire 54 then may be loaded into the distal portion of working lumen 26 at distal end 16 of catheter 12. When functional measurement wire 54 then is advanced proximally toward bifurcation 23, the proximal end of functional measurement wire 54 will be diverted into auxiliary lumen 28 via guiding member 82, as shown in FIG. 5A. Functional measurement wire 54 may be retracted proximally until the distal end of functional measurement wire 54 is disposed just proximal of bifurcation 23, as shown in FIG. 5B. Stylet 80 having guiding member 82 then may be removed from the proximal portion of working lumen 26.

The techniques described in FIGS. 3-5 hereinabove describe methods for loading functional measurement wire 54 into auxiliary lumen 28, so that functional measurement wire 54 readily may be advanced into the distal portion of the working lumen 26 and to a treatment site. It may be appreciated that functional measurement wire 54 also may be loaded into auxiliary lumen 28 using other techniques that are not illustrated. For example, the distal end of functional measurement wire 54 may be loaded into side port 30, then distally advanced within auxiliary lumen 28 until the distal end of functional measurement wire 54 is positioned just proximal of bifurcation 23.

Figure 6A:
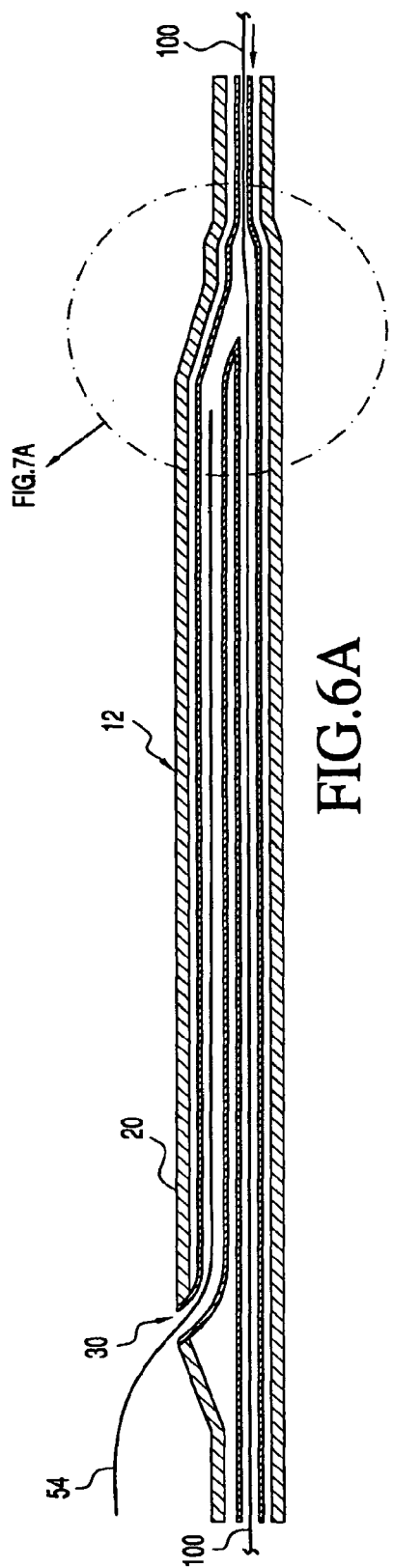
FIGS. 6A-6B are side sectional views depicting the selective use of the functional measurement wire in accordance with the present invention.

Referring to FIG. 6, a method for using the apparatus of the present invention during an intravascular procedure is described. In a first step, functional measurement wire 54 may be loaded into auxiliary lumen 28 and disposed just proximal to bifurcation 23, e.g., using one of the techniques described hereinabove with respect to FIGS. 3-5. Then, guidewire 100 having proximal and distal ends is provided, and the distal end of guidewire 100 is introduced into the patient's vasculature using techniques that are per se known in the art. The distal end of guidewire 100 then navigates a patient's vasculature and ultimately is disposed at a treatment site.

A physician then may advance the distal portion of working lumen 26 over the proximal end of guidewire 100, then distally advance catheter 12 to the vascular treatment site via guidewire 100. Once distal end 16 of catheter 12 is properly positioned, e.g., when balloon 32 is disposed within a stenosis, then balloon 32 may be inflated via inflation port 19 and inflation lumen 25.

Prior to inflation of balloon 32, or any time thereafter, a physician may obtain desired measurements at the treatment site using functional measurement wire 54. When measurements are desired, guidewire 100 may be retracted proximally within working lumen 26 until the distal end of guidewire 100 is positioned within a proximal portion of working lumen 26 located just proximal of bifurcation 23, as shown in FIG. 6B.

Figure 6B:
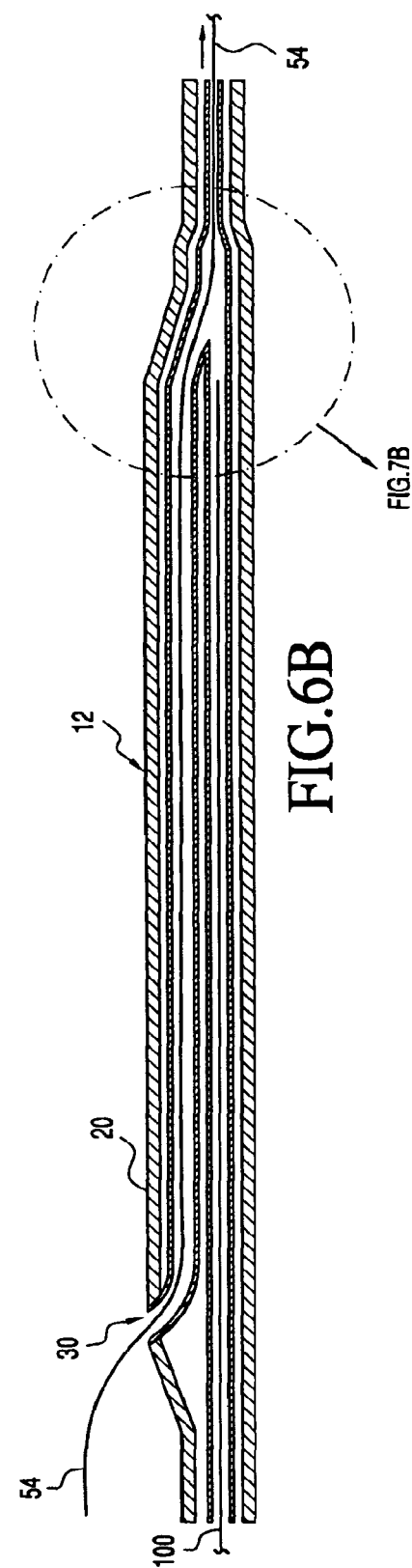

At this time, functional measurement wire 54 then may be advanced distally into the distal portion of working lumen 26 and toward distal end 16 of catheter 12, as shown in FIG. 6B. The distal end of functional measurement wire 54 may be advanced distal to catheter 12 via working lumen 26, to take the desired measurements near the treatment site. For example, functional measurement wire 54 may comprise a pressure or flow sensor at the distal end that enables pressure measurements to be obtained near a treatment site before, during or after an angioplasty procedure involving balloon 32.

Figure 7A:
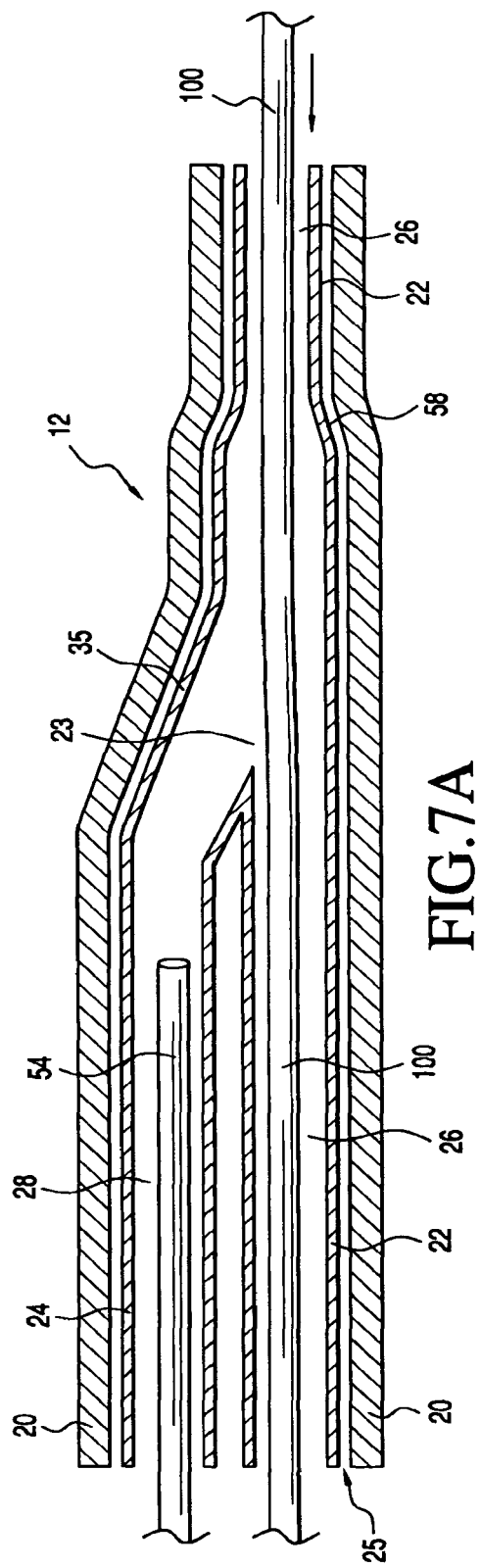
FIGS. 7A-7B are enlarged views of the schematics in FIGS. 6A-6B, respectively.
Figure 7B:
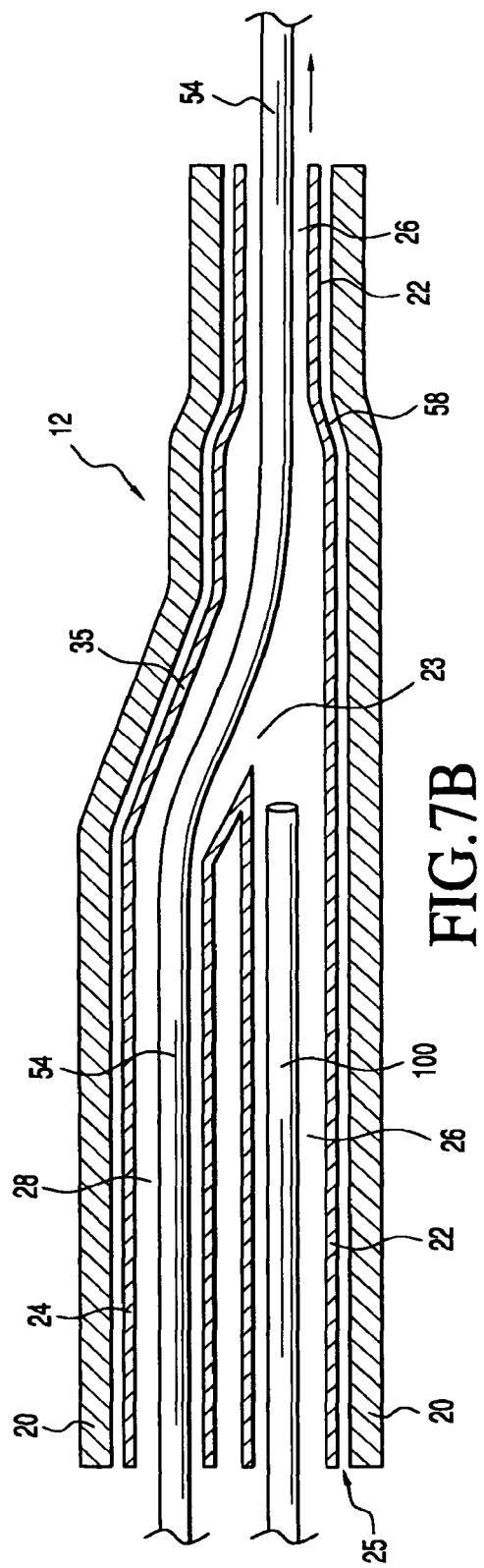

Referring to FIG. 7, a detailed schematic of FIG. 6 near bifurcation 23 is provided. In FIG. 7A, the distal end of functional measurement wire 54 is disposed within auxiliary lumen 28 at a location just proximal of bifurcation 23, e.g., according to one of the techniques described hereinabove with respect to FIGS. 3-5. A physician then may advance guidewire 100 to a vascular treatment site, then advance catheter 12 over guidewire 100 to the treatment site. Guidewire 100 then may be retracted proximally within working lumen 26 to a location just proximal of bifurcation 23, as shown in FIG. 7B.

Functional measurement wire 54 then may be advanced distally into the distal portion of working lumen 26 and toward the vascular treatment site, as shown in FIG. 7B. Taper 35, which provides a transition between inner tube 22 and auxiliary tube 24, facilitates guidance of functional measurement wire 54 into the distal portion of working lumen 26. Circumferential taper 58 of inner tube 22 further facilitates guidance of functional measurement wire 54 into the distal portion of working lumen 26, so that functional measurement wire 54 may be advanced distally to the vascular treatment site to obtain desired measurements.

Advantageously, after obtaining the desired measurements, functional measurement wire 54 may be retracted proximally and disposed in its original position within auxiliary lumen 28, as shown in FIG. 7A. Guidewire 100 then may be advanced distally into the distal portion of working lumen 26 and to the vascular treatment site, for example, to reposition distal end 16 of catheter 12 during the surgical procedure. In effect, the apparatus of the present invention allows both functional measurement wire 54 and guidewire 100 to be selectively advanced to a treatment site, to facilitate positioning of catheter 12 during a surgical procedure and efficiently obtain desired measurements at a treatment site.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

The invention claimed is:

1. An apparatus for facilitating the advancement of a functional measurement wire to a vascular treatment site, the apparatus comprising:
   an outer tube having proximal and distal ends;
   an inner tube having proximal and distal ends and a working lumen extending therethrough, the inner tube being disposed within the outer tube; and
   an auxiliary tube having proximal and distal ends and an auxiliary lumen extending therethrough, wherein the auxiliary lumen communicates at the proximal end with a side port disposed in a lateral surface of the outer tube and at a distal end communicates with the working lumen of the inner tube to define a bifurcation,
   wherein the auxiliary lumen is configured to permit the selective advancement of a functional measurement wire to a treatment site via a distal portion of the working lumen that is distal to the bifurcation.

2. The apparatus of claim 1 wherein a space between the inner tube and the outer tube forms an inflation lumen.

3. The apparatus of claim 2 further comprising a balloon affixed at a proximal point to the distal end of the outer tube and further affixed at a distal point to the distal end of the inner tube, wherein the balloon is in fluid communication with the inflation lumen.

4. The apparatus of claim 1 wherein the distal portion of the working lumen is configured to permit the longitudinal advancement of a guidewire.

5. The apparatus of claim 1 wherein the distal portion of the working lumen is configured to permit the longitudinal advancement of a functional measurement wire.

6. The apparatus of claim 1 further comprising a stylet having proximal and distal ends, and a receptor coupled to the distal end, wherein the receptor is adapted to engage a proximal end of the functional measurement wire to assist in positioning the functional measurement wire within the auxiliary lumen.

7. The apparatus of claim 6 wherein the receptor is adapted to be disposed in a region of inner tube that is situated just distal to the bifurcation.

8. The apparatus of claim 1 further comprising a tubular member that is fixedly disposed substantially within the auxiliary lumen at a location that is just proximal to the bifurcation.

9. The apparatus of claim 1 further comprising a stylet having proximal and distal ends and a guiding member coupled to the distal end, wherein the distal end of the stylet is configured to be advanced into a proximal end of the working lumen.

10. The apparatus of claim 9 wherein the guiding member is configured to direct a proximal end of the functional measurement wire into the auxiliary lumen.

11. The apparatus of claim 1 further comprising a taper that provides a transition between the inner tube and the auxiliary tube, the taper configured to facilitate the distal advancement of the functional measurement wire from the auxiliary lumen into the distal portion of the working lumen.

12. The apparatus of claim 1 further comprising a circumferential taper disposed just distal to the bifurcation, the circumferential taper configured to facilitate the distal advancement of the functional measurement wire from the auxiliary lumen into the distal portion of the working lumen.

13. The apparatus of claim 1 further comprising a functional measurement wire adapted to provide pressure or flow measurements.

14. A method for facilitating the advancement of a functional measurement wire to a vascular treatment site, the method comprising:
prov018ing apparatus comprising an outer tube having proximal and distal ends, an inner tube having proximal and distal ends and a working lumen extending therethrough, wherein the inner tube is disposed within the outer tube, and an auxiliary tube having proximal and distal ends and an auxiliary lumen extending therethrough, wherein the auxiliary lumen communicates at a proximal end with a side port disposed in a lateral surface of the outer tube and at a distal end communicates with the working lumen of the inner tube to define a bifurcation;
positioning a functional measurement wire within the auxiliary lumen;
advancing the apparatus to a treatment site over a guidewire disposed within the working lumen;
retracting the guidewire within the working lumen to a location proximal of the bifurcation; and
selectively advancing the functional measurement wire into the working lumen to obtain measurements near the treatment site.

15. The method of claim 14 wherein positioning the functional measurement wire within the auxiliary lumen further comprises:
providing a stylet having proximal and distal ends a receptor coupled to the distal end;
loading the distal end of the stylet into the side port and disposing the distal end substantially within the working lumen;
causing the proximal end of the functional measurement wire to engage the receptor; and
proximally retracting the stylet to cause the functional measurement wire to be guided into the auxiliary lumen.

16. The method of claim 14 wherein positioning the functional measurement wire within the auxiliary lumen further comprises:
providing a stylet having proximal and distal ends a guiding member coupled to the distal end;
positioning the guiding member within the working lumen at a position just proximal of the bifurcation; and
causing the proximal end of the functional measurement wire to be directed into the auxiliary lumen.

17. The method of claim 14 wherein positioning the functional measurement wire within the auxiliary lumen further comprises:
providing a tubular member that is fixedly disposed substantially within the auxiliary lumen at a location just proximal of the bifurcation; and
causing the proximal end of the functional measurement wire to be advanced through the tubular member and directed into the auxiliary lumen.

18. The method of claim 17 wherein causing the proximal end of the functional measurement wire to be advanced through the tubular member and directed into the auxiliary lumen comprises compressing the outer tube near the bifurcation.

19. The method of claim 14 wherein positioning the functional measurement wire within the auxiliary lumen further comprises:
advancing a distal end of the functional measurement wire into the auxiliary lumen via the side port; and
distally advancing the distal end of the functional measurement wire within the auxiliary lumen.

20. The method of claim 14 wherein obtaining measurements near the treatment site includes obtaining pressure measurements.

* * * * *